(12) United States Patent
Sekido

(10) Patent No.: US 9,520,212 B2
(45) Date of Patent: Dec. 13, 2016

(54) ALIGNED STRUCTURE OF CABLES AND PRODUCTION METHOD OF ALIGNED STRUCTURE OF CABLES

(71) Applicant: OLYMPUS CORPORATION, Tokyo (JP)

(72) Inventor: Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 13 days.

(21) Appl. No.: 14/088,854

(22) Filed: Nov. 25, 2013

(65) Prior Publication Data

US 2014/0144697 A1 May 29, 2014

(30) Foreign Application Priority Data

Nov. 26, 2012 (JP) .................................. 2012-257824

(51) Int. Cl.
*H01B 13/06* (2006.01)
*A61B 1/00* (2006.01)
*A61B 1/05* (2006.01)

(52) U.S. Cl.
CPC ............. *H01B 13/06* (2013.01); *A61B 1/0011* (2013.01); *A61B 1/00114* (2013.01);
(Continued)

(58) Field of Classification Search
USPC .......... 600/110; 174/76, 74 A, 93, 97, 117 F, 174/52.2, 75 R, 70 R
See application file for complete search history.

(56) References Cited

U.S. PATENT DOCUMENTS 5,212,348 A * 5/1993 Gibson .................. H01R 43/28
174/117 F
5,281,762 A * 1/1994 Long .................... H01R 9/0515
174/117 F (Continued)

FOREIGN PATENT DOCUMENTS

JP H08-330003 A 12/1996
JP 2003-178826 A 6/2003
(Continued)

OTHER PUBLICATIONS

English Abstract only of JP 09-090237 dated Apr. 4, 1997.
Japanese Office Action dated May 31, 2016 in related Japanese Patent Application No. 2012-257824.

*Primary Examiner* — Timothy Thompson
*Assistant Examiner* — Michael F McAllister
(74) *Attorney, Agent, or Firm* — Scully, Scott, Murphy & Presser, P.C.

(57) ABSTRACT

An aligned structure of cables includes: a plurality of cables each including a conductive cable core, an insulator covering an outer periphery of the cable core, and a cable core exposed portion, in which the cable core is exposed, on a side of a distal end of the cable; a first cable core aligning insulator including a plurality of grooves into which the cable core exposed portions of the cables are respectively fitted and which align the cable cores; and a cable core fixing insulator which fixes the cable core exposed portions aligned by the first cable core aligning insulator, wherein cross sections of the cable cores are exposed on a surface on a side of distal ends of the cable cores of the cable core fixing insulator, and a pitch of the cross sections is shorter than a pitch of the cables.

6 Claims, 12 Drawing Sheets

(52) U.S. Cl.
CPC .......... *A61B 1/00124* (2013.01); *A61B 1/051* (2013.01); *Y10T 29/49826* (2015.01)

(56) References Cited

U.S. PATENT DOCUMENTS

| | | | | |
|---|---|---|---|---|
| 5,377,286 | A * | 12/1994 | Iida | G02B 6/2931 385/115 |
| 5,815,621 | A * | 9/1998 | Sakai | B24B 19/226 264/1.1 |
| 5,878,285 | A * | 3/1999 | Wilk | G03B 17/04 396/200 |
| 5,879,285 | A * | 3/1999 | Ishii | 600/110 |
| 8,580,162 | B2 * | 11/2013 | Ott | B29D 11/0075 264/1.25 |
| 8,878,062 | B2 * | 11/2014 | Tanaka | H01R 4/027 174/71 C |
| 2001/0022234 | A1 * | 9/2001 | Okumura | H01R 9/0512 174/78 |
| 2003/0026550 | A1 * | 2/2003 | Demangone | G02B 6/3834 385/78 |
| 2005/0180702 | A1 * | 8/2005 | Kevern | G02B 6/3885 385/93 |
| 2009/0101408 | A1 * | 4/2009 | Koyama | H01R 9/0506 174/72 A |
| 2012/0103686 | A1 * | 5/2012 | Sekido | A61B 1/00 174/75 R |

FOREIGN PATENT DOCUMENTS

| | | |
|---|---|---|
| JP | 2003-208937 A1 | 7/2003 |
| JP | 3863583 B2 | 12/2006 |

\* cited by examiner

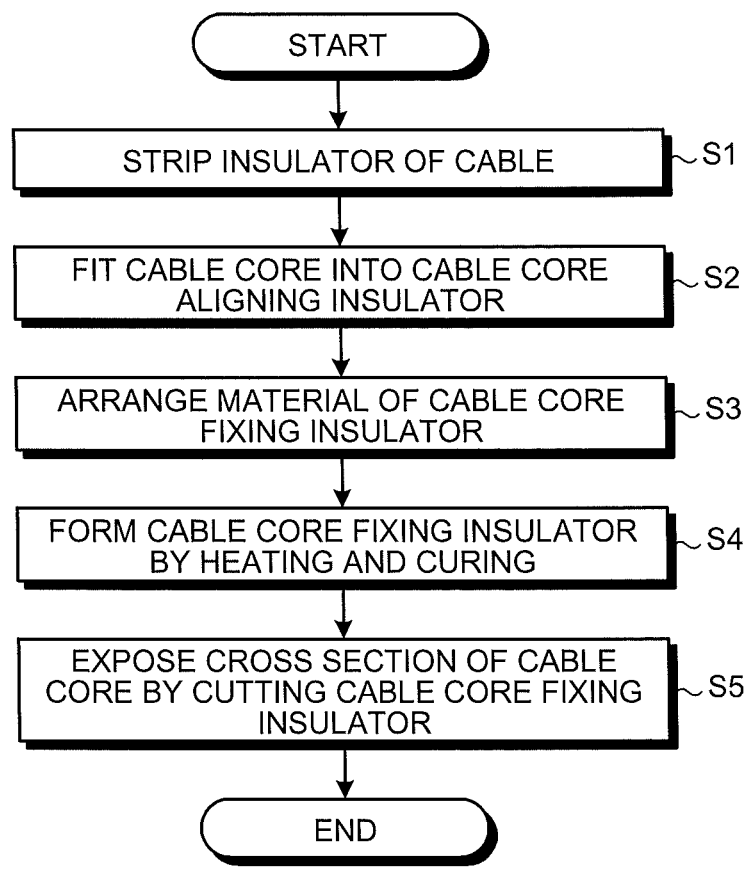

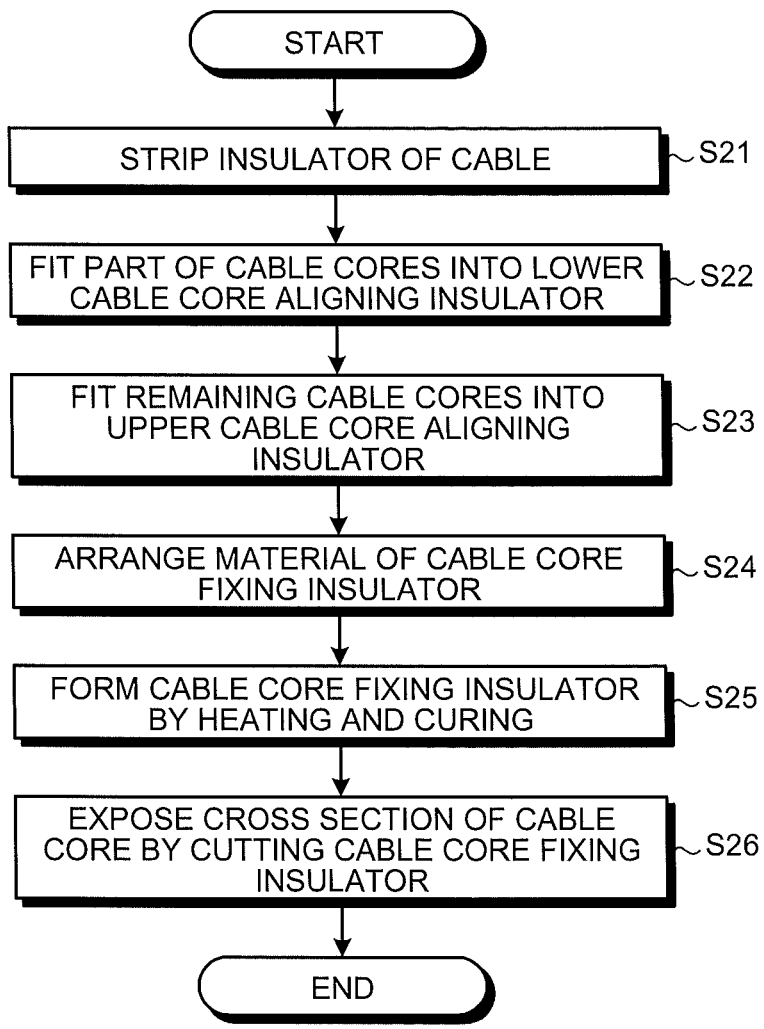

ALIGNED STRUCTURE OF CABLES AND PRODUCTION METHOD OF ALIGNED STRUCTURE OF CABLES

CROSS-REFERENCE TO RELATED APPLICATIONS

This application is based upon and claims the benefit of priority from Japanese Patent Application No. 2012-257824, filed on Nov. 26, 2012, the entire contents of which are incorporated herein by reference.

BACKGROUND OF THE INVENTION

1. Field of the Invention

This invention relates to an aligned structure of cables and a production method of the aligned structure of cables.

2. Description of the Related Art

Recently, medical and industrial endoscopes have been widely used. As the medical endoscope, for example, there is one including an imaging device which includes an imaging element, such as a CCD, at a distal end of an insertion unit to be inserted into a body. By inserting the insertion unit deeply into a body, a lesion can be observed. Furthermore, by using the medical endoscope together with a treatment tool when needed, an exam and a treatment of the body can be performed.

In such an endoscope, to display an image on a monitor, image information imaged by the imaging element is converted into an electric signal and transmitted to a signal processing device through a signal wire. In the signal processing device, signal processing is performed. The imaging element in the endoscope and the signal processing device are connected by a combined cable, in which a plurality of cables are combined, to transmit an image signal and a clock signal, and to provide a drive power source to the imaging element, for example.

As a technique related to connection of a combined cable, a technique to connect a combined cable including a plurality of coaxial cables collectively to a circuit board including electrodes, is disclosed (for example, see Japanese Patent No. 3863583).

SUMMARY OF THE INVENTION

An aligned structure of cables according to one aspect of the present invention includes: a plurality of cables each including a conductive cable core, an insulator covering an outer periphery of the cable core, and a cable core exposed portion, in which the cable core is exposed, on a side of a distal end of the cable; a first cable core aligning insulator including a plurality of grooves into which the cable core exposed portions of the cables are respectively fitted and which align the cable cores; and a cable core fixing insulator which fixes the cable core exposed portions aligned by the first cable core aligning insulator, wherein cross sections of the cable cores are exposed on a surface on a side of distal ends of the cable cores of the cable core fixing insulator, and a pitch of the cross sections is shorter than a pitch of the cables.

A production method of an aligned structure of cables according to one aspect of the present invention includes: aligning conductive cable cores by respectively fitting, into a plurality of grooves of a first cable core aligning insulator and a second cable core aligning insulator, cable core exposed portions, in which the cable cores are exposed on a side of distal ends, of a plurality of cables each including the cable core and an insulator covering an outer periphery of the cable core; fixing the cable cores by arranging a material of a cable core fixing insulator on a peripheral portion of the cable core exposed portions aligned by the first cable core aligning insulator and the second cable core aligning insulator, and by curing the material by heating; and exposing cross sections of the cable cores by cutting the cable core fixing insulator or the second cable core aligning insulator in a direction vertical to a longitudinal direction of the cable cores at an intended position of the cable core fixing insulator or the second cable core aligning insulator, wherein a pitch of the cross sections of the cable cores is shorter than a pitch of the cables.

A production method of an aligned structure of cables according to one aspect of the present invention includes: a first aligning step including aligning conductive cable cores, for a part of a plurality of cables each including the cable core and an insulator covering an outer periphery of the cable core, by respectively fitting cable core exposed portions in which the cable cores are exposed on a side of distal ends, into a plurality of grooves of a lower first cable core aligning insulator and a lower second cable core aligning insulator; a second aligning step including aligning the cable cores, for the remaining part of the cables, by respectively fitting the cable core exposed portions into a plurality of grooves of an upper first cable core aligning insulator and an upper second cable core aligning insulator which are stacked and arranged on the lower first cable core aligning insulator and the lower second cable core aligning insulator, respectively; fixing the cable cores by arranging a material of a cable core fixing insulator on a peripheral portion of the cable core exposed portions stacked vertically in the first aligning step and the second aligning step and by curing the material by heating; and exposing cross sections of the cable cores by cutting the cable core fixing insulator or the second cable core aligning insulator in a direction vertical to a longitudinal direction of the cable cores at an intended position of the cable core fixing insulator or the second cable core aligning insulator, wherein a pitch of the cross sections of the cable cores is shorter than a pitch of the cables.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a flowchart of production steps of the aligned structure of cables according to the first embodiment of the present invention;

FIG. 10 is a flowchart of production steps of the aligned structure of cables according to the third embodiment of the present invention;

DETAILED DESCRIPTION OF THE PREFERRED EMBODIMENTS

In the following, embodiments of the present invention will be described in detail with reference to the drawings. Note that the present invention is not limited to the following embodiments. Also, each figure referred to in the following descriptions illustrates a shape, a size, and a positional relationship schematically to make it easy to understand contents of the present invention. That is, the present invention is not limited to a shape, a size, and a positional relationship illustrated as an example in each figure.

Figure 1:
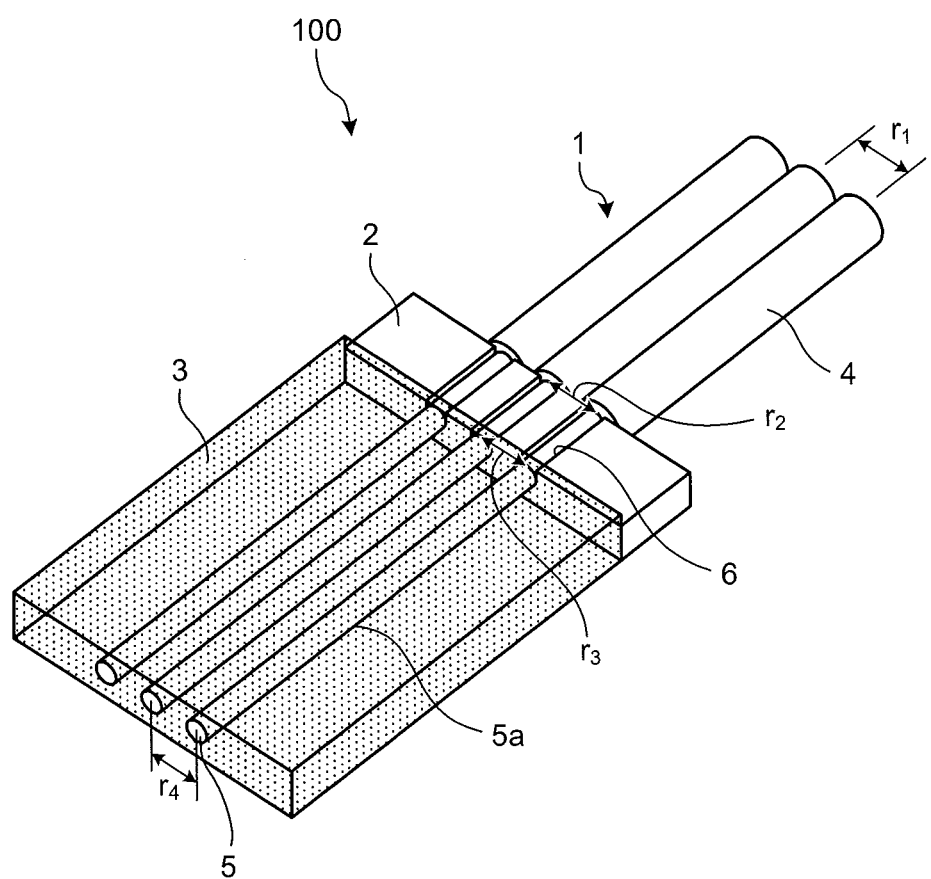
FIG. 1 is a perspective view illustrating an aligned structure of cables according to a first embodiment of the present invention.

First, an aligned structure of cables according to a first embodiment will be described. FIG. 1 is a perspective view illustrating the aligned structure of cables according to the first embodiment of the present invention. As illustrated in FIG. 1, an aligned structure of cables 100 according to the first embodiment includes three cables 1, a first cable core aligning insulator 2 which aligns cable cores 5 of the cables 1, and a cable core fixing insulator 3 which fixes the cable cores 5.

The cables 1 include the conductive cable cores 5, and insulators 4 which cover outer peripheries of the cable cores 5. On the side of distal ends of the cables 1, the insulators 4 are stripped over a prescribed length and cable core exposed portions $5a$, in which the cable cores 5 are exposed, are formed.

The first cable core aligning insulator 2 includes, on an upper surface portion thereof, grooves 6 into which the cable core exposed portions $5a$ are fitted. The grooves 6 are formed in the same number as the cables 1 to be aligned. As a material to form the first cable core aligning insulator 2, an insulating resin is selected. Considering workability and the like of the grooves 6, engineering plastics, such as polyacetal, can be preferably used.

The cable core fixing insulator 3 fixes the cable core exposed portions $5a$ aligned by the first cable core aligning insulator 2. The cable core fixing insulator 3 includes thermosetting resin. Note that instead of the thermosetting resin, photo-curing resin such as ultraviolet-curing resin, or air-setting resin may be used. In the following, a case of using the thermosetting resin will be described. The cable core fixing insulator 3 preferably includes epoxy resin and the like, which are insulators and have good adhesiveness to the material of the first cable core aligning insulator 2. When the aligned structure of cables 100 is connected to a board and the like, the cable core fixing insulator 3 is attached by being gripped with a fixture or the like. Therefore, opposing side surfaces of the cable core fixing insulator 3 are preferably formed substantially parallel to each other. Also, cross sections of the cable cores 5 are exposed on a surface on the side of distal ends of the cable cores of the cable core fixing insulator 3. The exposed cable cores 5 are connected to electrodes of a printed board and the like by heating and melting solder and the like. There may be a case where the cable core fixing insulator 3 expands due to heating adhesion and positions of the cross sections of the cable cores 5 are changed, whereby the connection fails. Therefore, a coefficient of expansion of the cable core fixing insulator 3 is preferably similar to a coefficient of thermal expansion of a material to be connected, or as small as possible.

A pitch $r_4$ is formed to be shorter than a pitch $r_1$. The pitch $r_4$ is a pitch of the exposed cross sections of the cable cores 5 of the cable core fixing insulator 3. The pitch $r_1$ is a pitch between the cables 1. In the aligned structure of cables 100 according to the first embodiment, it is preferable for the pitch $r_4$ to be substantially the same as a pitch $r_2$ and a pitch $r_3$. The pitch $r_2$ is a pitch of the cable cores 5 on the side of the cables 1 of the first cable core aligning insulator 2. The pitch $r_3$ is a pitch of the cable cores 5 on the side of the cable core fixing insulator 3 of the first cable core aligning insulator 2. That is, relationships among the pitches preferably satisfy $r_4=r_3=r_2<r_1$. In this case, it is necessary to narrow down a pitch of the cable cores 5 between end surfaces of the cables 1 and the first cable core aligning insulator 2. However, the grooves 6 of the first cable core aligning insulator 2 can be made parallel to each other. Alternatively, the pitch $r_4$ and the pitch $r_3$ are preferably formed the same, and the pitch $r_1$ and the pitch $r_2$ are preferably formed the same. That is, relationships among the pitches preferably satisfy $r_4=r_3<r_2=r_1$. In this case, the cable cores 5 can be made parallel to each other between the end surfaces of the cables 1 and the first cable core aligning insulator 2. However, the grooves 6 of the first cable core aligning insulator 2 cannot be made parallel, since it is necessary to make the pitch on the side of the cable core fixing insulator 3 narrower than the pitch on the side of the cables 1. In each case, by at least making the pitch $r_4$ and the pitch $r_3$ the same, a pitch of the cable cores 5 in the cable core fixing insulator 3 becomes constant and it becomes easier to control the pitch $r_4$.

Next, a production method of the aligned structure of cables 100 according to the first embodiment will be described with reference to FIG. 2 and FIGS. 3A to 3E. FIG. 2 is a flowchart of production steps of the aligned structure of cables according to the first embodiment of the present invention. FIGS. 3A to 3E are schematic views for describing the production steps of the aligned structure of cables according to the first embodiment of the present invention.

First, by stripping the insulators 4 of the cables 1 over a prescribed length (step S1), the cable core exposed portions 5a are formed.

Figure 3A:
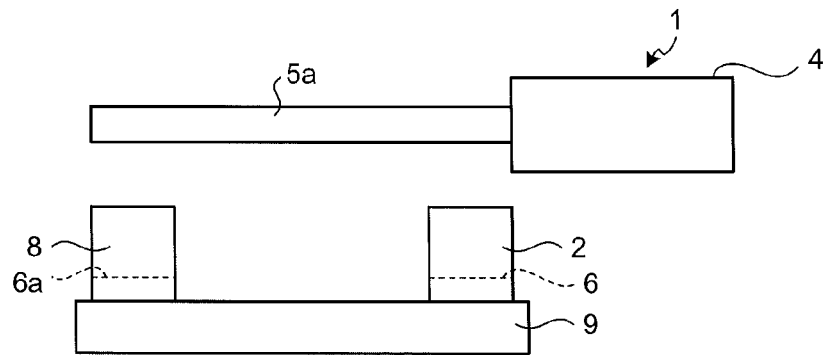
FIG. 3A is a schematic view for describing a production step of the aligned structure of cables according to the first embodiment of the present invention.
Figure 3B:
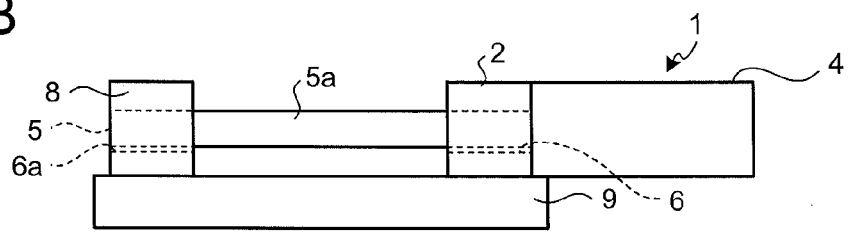
FIG. 3B is a schematic view for describing a production step of the aligned structure of cables according to the first embodiment of the present invention.

As illustrated in FIG. 3A, the first cable core aligning insulator 2 and a second cable core aligning insulator 8 are arranged on a prescribed lower mold 9, and the cables 1 are aligned by fitting the cable core exposed portions 5a into grooves 6 and 6a (step S2, see FIG. 3B). Note that it is preferable to design the shapes of the grooves 6 and 6a to prevent the cable core exposed portions 5a from sagging, or to add tensile stress to prevent the cable core exposed portions 5a from sagging.

Figure 3C:
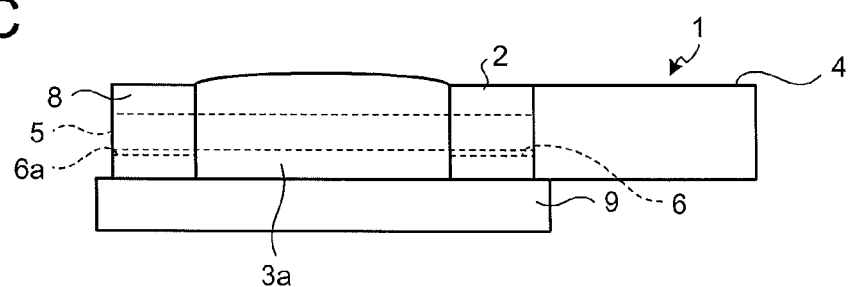
FIG. 3C is a schematic view for describing a production step of the aligned structure of cables according to the first embodiment of the present invention.

Next, as illustrated in FIG. 3C, a material 3a of the cable core fixing insulator 3 is arranged, for example by being applied, on the periphery of the cable core exposed portions 5a aligned by the first cable core aligning insulator 2 and the second cable core aligning insulator 8 (step S3).

Figure 3D:
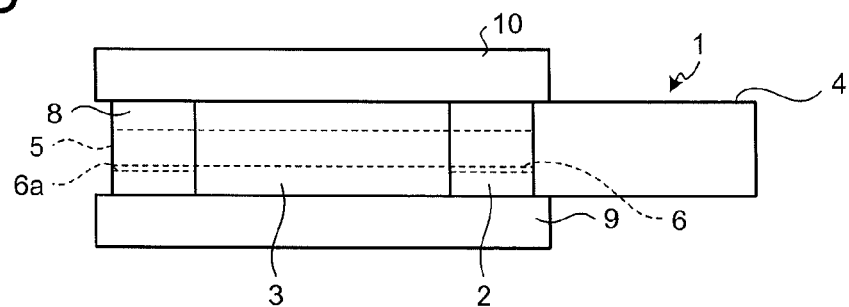
FIG. 3D is a schematic view for describing a production step of the aligned structure of cables according to the first embodiment of the present invention.

Then, as illustrated in FIG. 3D, the material 3a of the cable core fixing insulator 3 is fixed by an upper mold 10 and heated at an intended temperature. As a result, the material is cured and the cable core fixing insulator 3 is formed (step S4).

Figure 3E:
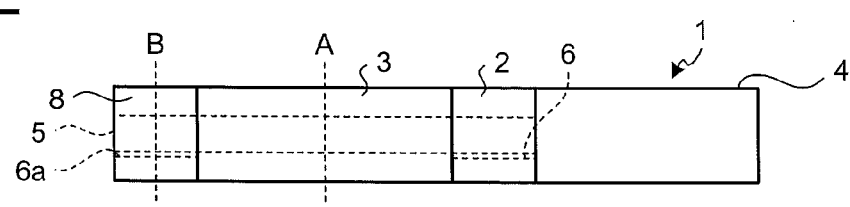
FIG. 3E is a schematic view for describing a production step of the aligned structure of cables according to the first embodiment of the present invention.

After the heating and curing, as illustrated in FIG. 3E, the upper mold 10 and the lower mold 9 are removed and the cable core fixing insulator 3 is cut, at the position of the line A, in a direction vertical to the longitudinal direction of the cable cores 5. In this manner, the aligned structure of cables 100, in which the cross sections of the cable cores 5 are exposed, is produced (step S5). Note that the aligned structure of cables 100 may be produced without using the second cable core aligning insulator 8, as long as the cable core exposed portions 5a are not sagged.

In the aligned structure of cables 100 according to the first embodiment, the pitch $r_4$ between the cable cores 5 can be made smaller than the pitch $r_1$ between the cables 1. Thus, the size of the aligned structure of cables 100 can be made further smaller.

Note that in the aligned structure of cables 100 described in the first embodiment, the three cables 1 have been aligned. However, in the first embodiment, the number of aligned cables 1 is not limited to three, as long as the pitch $r_4$ between the cable cores 5 can be made smaller than the pitch $r_1$ between the cables 1.

Furthermore, in the aligned structure of cables 100 produced by the production method of the aligned structure of cables according to the first embodiment, the first cable core aligning insulator 2 is fixed by the adhesion with the cable core fixing insulator 3. However, even when the first cable core aligning insulator 2 is removed, insulation quality can be secured by a sealant and the like. Also, since the pitch $r_4$ between the cable cores 5 is smaller than the pitch $r_1$ between the cables 1, connection with another semiconductor part and the like can be performed without any problem.

Figure 4:
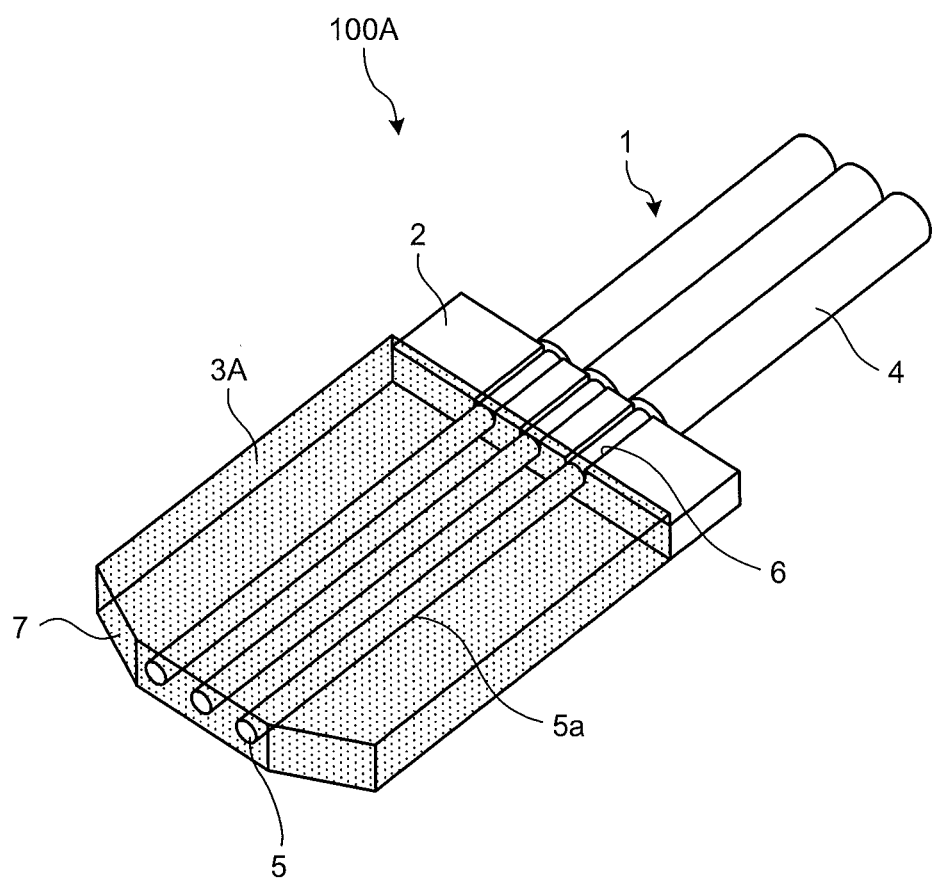
FIG. 4 is a perspective view illustrating an aligned structure of cables according to a modified example of the first embodiment of the present invention.

In addition, in the aligned structure of cables 100 according to the first embodiment, it is preferable to form beveled portions on a flat surface, on which the cross sections of the cable cores 5 are exposed, of the cable core fixing insulator 3. FIG. 4 is a perspective view illustrating an aligned structure of cables according to a modified example of the first embodiment of the present invention.

In an aligned structure of cables 100A according to the modified example, beveled portions 7 are formed on both ends in an alignment direction of an end surface, on which cross sections of the cable cores 5 are exposed, of the cable core fixing insulator 3. The beveled portions 7 may be formed by being beveled after a cable core fixing insulator 3A is cut in a vertical direction in step S5 of the production steps.

Figure 5A:
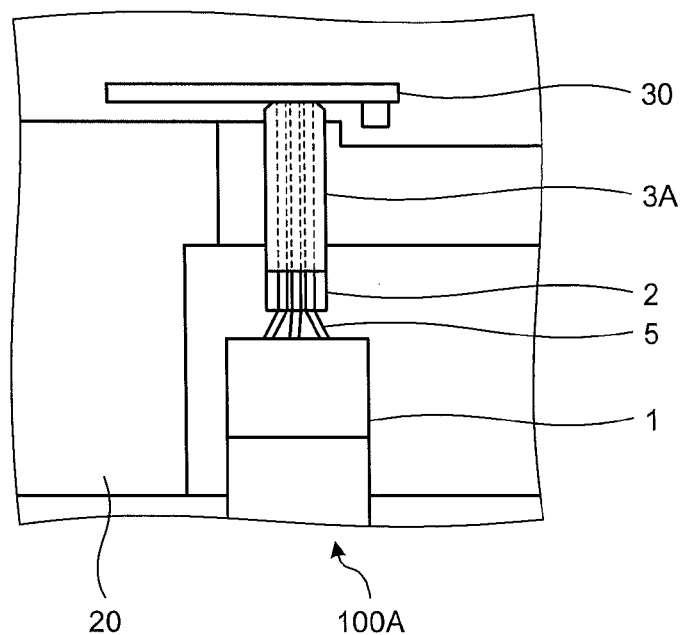
FIG. 5A is a schematic view for describing connection of the aligned structure of cables to an imaging module according to the modified example of the first embodiment of the present invention.
Figure 5B:
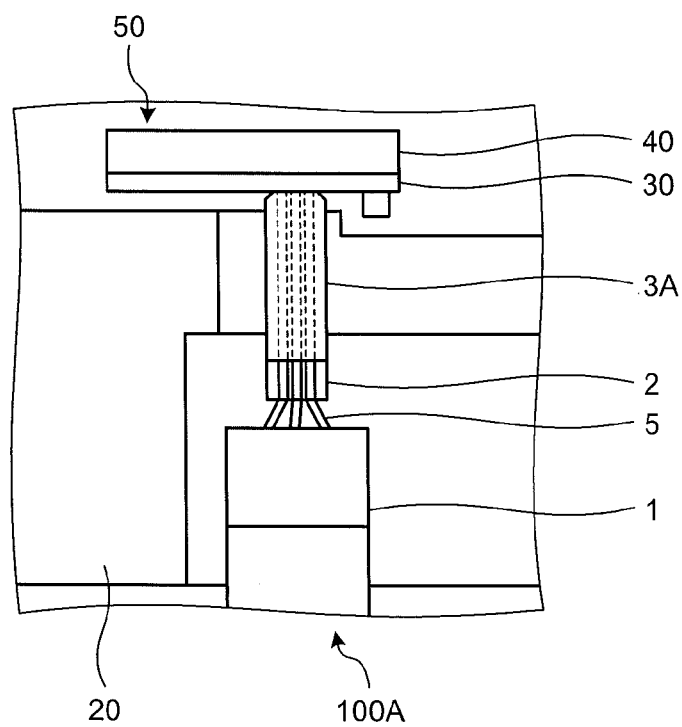
FIG. 5B is a schematic view for describing the connection of the aligned structure of cables to the imaging module according to the modified example of the first embodiment of the present invention.

FIGS. 5A and 5B are schematic views for describing connection of the aligned structure of cables to an imaging module, according to the modified example of the first embodiment of the present invention. When connected to a printed board 30 in order to produce a semiconductor device 50, first, as illustrated in FIG. 5A, the aligned structure of cables 100A is gripped by a clamp-type fixture 20 on the opposing surfaces of the cable core fixing insulator 3A, which are parallel to a longitudinal direction of the cables 1. During the connection, the cable core fixing insulator 3A may be preheated through the clamp-type fixture 20 and the heated cable core fixing insulator 3A may be deformed. When the beveled portions 7 are not formed, among the surfaces of the cable core fixing insulator 3A, if the surface (especially peripheral part) on which the cross sections of the cable cores 5 are exposed is deformed by the heating, the contact between the cross sections of the cable cores 5 and the electrodes of the printed board 30 may be interfered with. In the aligned structure of cables 100A according to the modified example, the beveled portions 7 are formed on the surface on which the cross sections of the cable cores 5 are exposed and which is a connection surface with the printed board 30 and the like. Thus, even when the cable core fixing insulator 3A is deformed, the contact between the cable cores 5 and the electrodes and the like of the printed board 30 is not interfered with. Therefore, connection failure can be prevented.

Note that as illustrated in FIG. 5A, after the aligned structure of cables 100A is connected to the printed board 30 by the solder and the like, the semiconductor device 50 is produced by connecting an imaging element 40 and the like to a rear surface of the printed board 30 (see FIG. 5B). The solder used to connect the aligned structure of cables 100A and the printed board 30 preferably has a higher melting point than the solder used to connect the printed board 30 and the imaging element 40. By using the solder of the higher melting point first, remelting of the connected portion of the aligned structure of cables 100A can be prevented.

Figure 6:
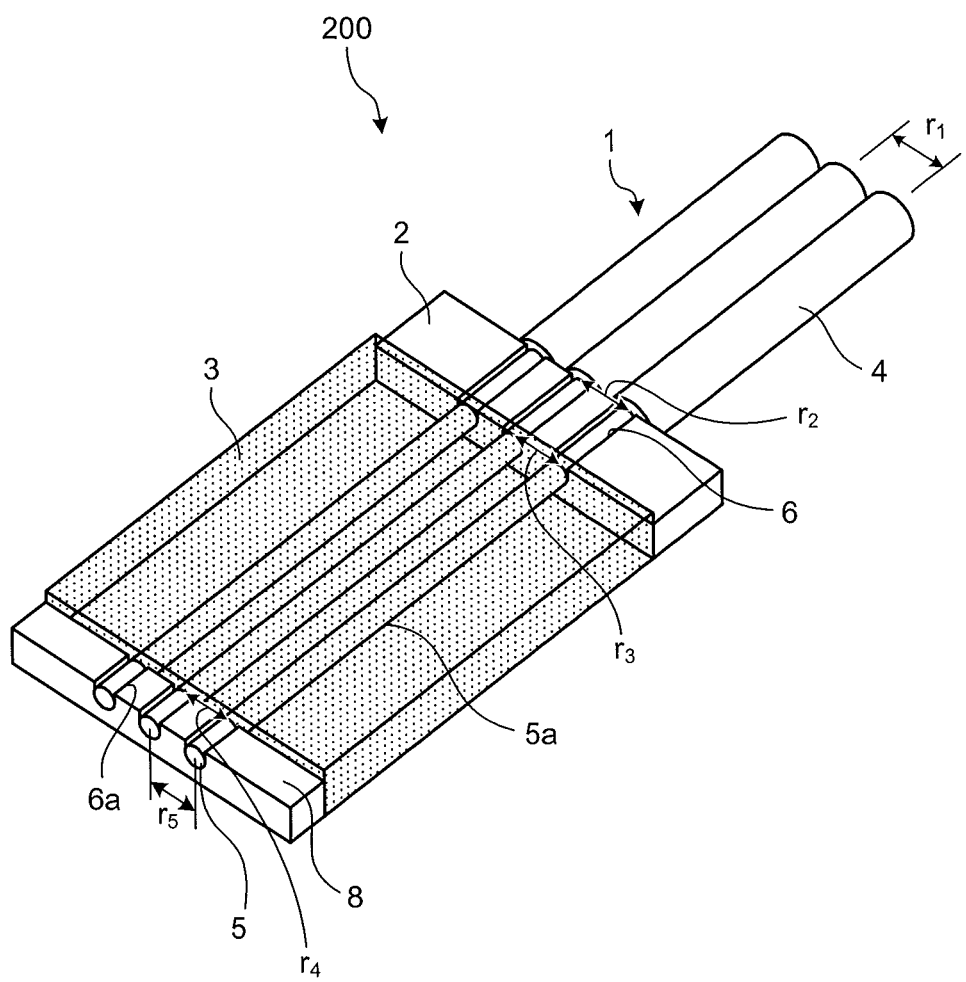
FIG. 6 is a perspective view illustrating an aligned structure of cables according to a second embodiment of the present invention.

An aligned structure of cables according to a second embodiment will be described. FIG. 6 is a perspective view illustrating the aligned structure of cables according to the second embodiment of the present invention.

The aligned structure of cables 200 according to the second embodiment differs from the aligned structure of cables 100 according to the first embodiment in including a second cable core aligning insulator 8. The second cable core aligning insulator 8 is arranged on the opposite side of a first cable core aligning insulator 2 across a cable core fixing insulator 3. The second cable core aligning insulator 8 includes grooves 6a into which cable core exposed portions 5a are fitted and is formed of the same material as the first cable core aligning insulator 2, for example, polyacetal. Cross sections of cable cores 5 are exposed on a surface of the second cable core aligning insulator 8, which surface is on the opposite side of the surface contacting the cable core fixing insulator 3. The exposed cable cores 5 are connected to electrodes of a printed board by solder, for example. There may be a case where the second cable core aligning insulator 8 expands due to heating adhesion by the solder and the like and positions of the cross sections of the cable cores 5 are changed, whereby the connection fails. Therefore, a coefficient of expansion of the second cable core aligning insulator 8 is preferably similar to a coefficient of thermal expansion of a material to be connected, or as small as possible.

In the aligned structure of cables 200 according to the second embodiment, a pitch $r_5$ is formed to be shorter than a pitch $r_1$. The pitch $r_5$ is a pitch of the cross sections of the cable cores 5, the cross sections being exposed on the flat surface of the second cable core aligning insulator 8. The pitch $r_1$ is a pitch of the cables 1. The pitch $r_5$ only needs to be the same as a pitch $r_4$. The pitch $r_4$ is a pitch of cross sections of the cable cores 5 on the side of the second cable core aligning insulator 8 of the cable core fixing insulator 3. A pitch $r_2$ and a pitch $r_3$ may be the same length as the pitch $r_5$ or the pitch $r_1$, as long as the pitch $r_2$ and the pitch $r_3$ are equal to or longer than the pitch $r_5$ and equal to or shorter than the pitch $r_1$. The pitch $r_2$ is a pitch of cross sections of the cable cores 5 on the side of the cables 1 of the first cable core aligning insulator 2. The pitch $r_3$ is a pitch of cross sections of the cable cores 5 on the side of the cable core fixing insulator 3 of the first cable core aligning insulator 2. By making the pitch $r_5$ and the pitch $r_4$ the same, a pitch of cross sections of the cable cores 5 in the second cable core aligning insulator 8 becomes constant and it becomes easier to control the pitch $r_5$.

Figure 7:
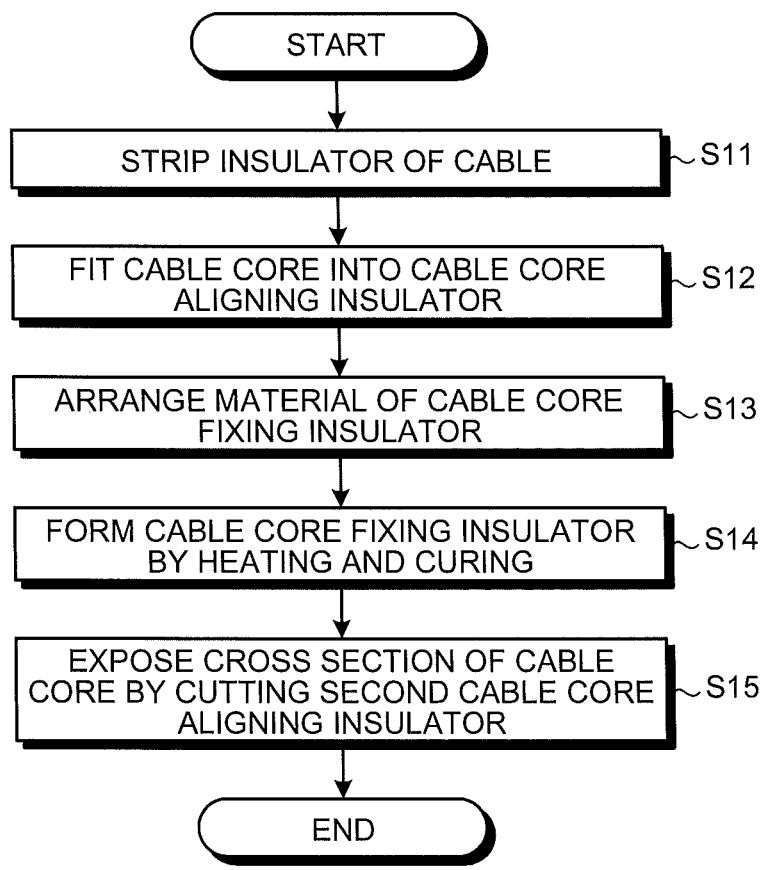
FIG. 7 is a flowchart of production steps of the aligned structure of cables according to the second embodiment of the present invention.

Next, a production method of the aligned structure of cables 200 according to the second embodiment will be described with reference to FIG. 7 and FIGS. 3A to 3E. FIG. 7 is a flowchart of production steps of the aligned structure of cables according to the second embodiment of the present invention.

First, like steps S1 to S4 of the production steps of the aligned structure of cables 100 according to the first embodiment, by stripping insulators 4 of the cables 1 over a prescribed length (step S11), the cable core exposed portions 5a are formed. Then, by fitting the cable core exposed portions 5a into grooves 6 of the first cable core aligning insulator 2 and the grooves 6a of the second cable core aligning insulator 8, the cables 1 are aligned (step S12). After a material of the cable core fixing insulator 3 is applied and arranged in the periphery of the cable core exposed portions 5a (step S13), the cable core fixing insulator 3 is formed by being heated and cured at an intended temperature (step S14).

After the heating and curing, the second cable core aligning insulator 8 is cut, in a vertical direction, at a position of the line B illustrated in FIG. 3E, and the aligned structure of cables 200, in which the cross sections of the cable cores 5 are exposed, is produced (step S15).

In the aligned structure of cables 200 according to the second embodiment, the pitch $r_5$ between the cable cores 5 can be made smaller than the pitch $r_1$ between the cables 1.

Thus, the size of the aligned structure of cables 200 can be made further smaller. In addition, in the aligned structure of cables 200, since the pitch of the cross sections of the cable cores 5 can be set by the grooves 6a of the second cable core aligning insulator 8 in advance, positional accuracy of the cross sections of the cable cores 5 can be improved.

Figure 8:
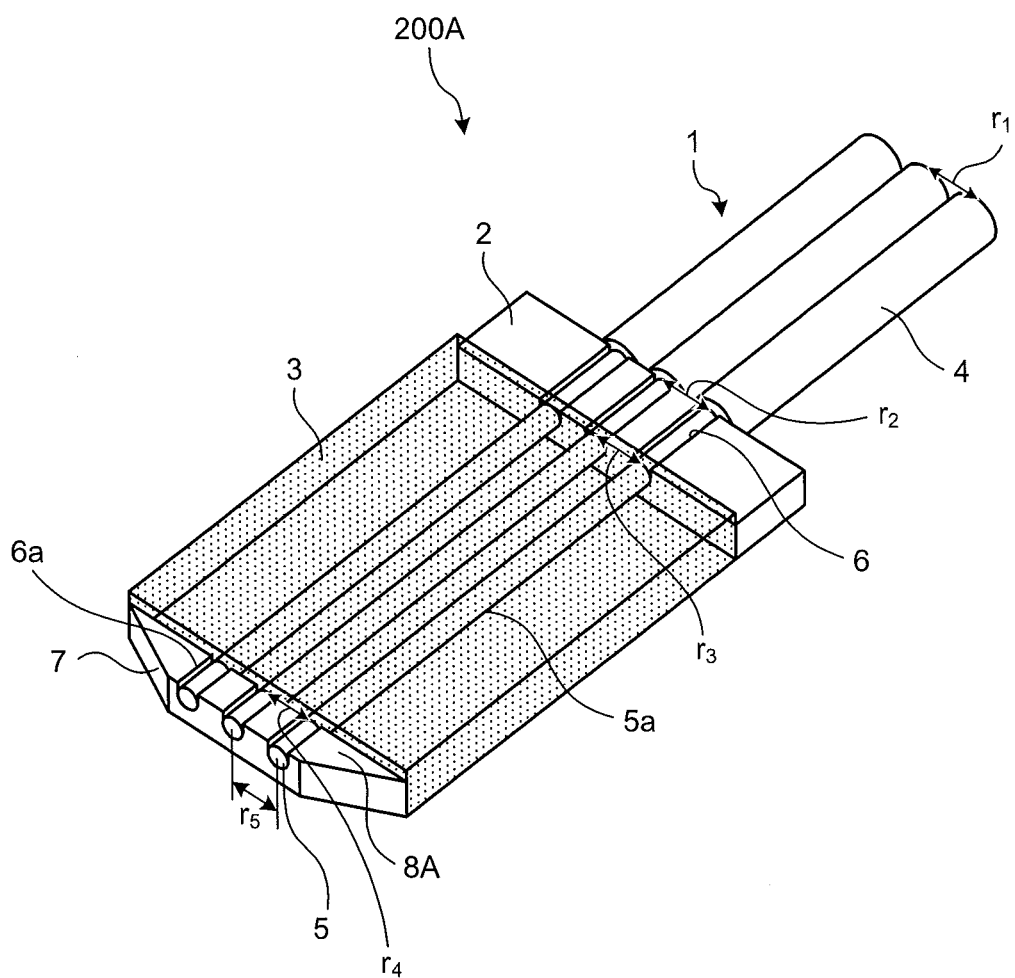
FIG. 8 is a perspective view illustrating an aligned structure of cables according to a modified example of the second embodiment of the present invention.

Also, in the aligned structure of cables 200 according to the second embodiment, a beveled portion may be formed on a flat surface, on which the cross sections of the cable cores 5 are exposed, of the second cable core aligning insulator 8. FIG. 8 is a perspective view illustrating an aligned structure of cables according to a modified example of the second embodiment of the present invention.

In an aligned structure of cables 200A according to the modified example, beveled portions 7 are formed on both ends in an alignment direction of an end surface, on which cross sections of the cable cores 5 are exposed, of a second cable core aligning insulator 8A. The beveled portions 7 may be formed by being beveled after the second cable core aligning insulator 8 is cut in the vertical direction in step S15, or a second cable core aligning insulator on which the beveled portions 7 have been already formed may be used.

Figure 9:
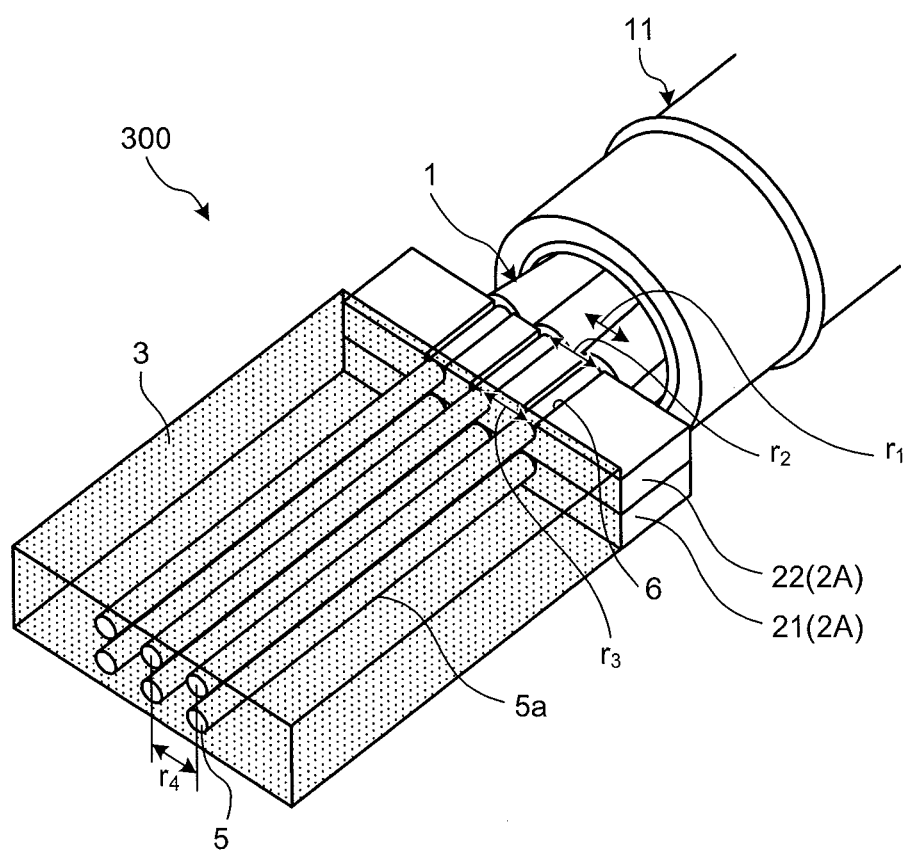
FIG. 9 is a perspective view illustrating an aligned structure of cables according to a third embodiment of the present invention.

An aligned structure of cables according to a third embodiment will be described. FIG. 9 is a perspective view illustrating the aligned structure of cables according to the third embodiment of the present invention. In an aligned structure of cables 300 according to the third embodiment, cable cores 5 of cables 1 are aligned by being stacked in two tiers. In this respect, the aligned structure of cables 300 according to the third embodiment differs from the aligned structure of cables 100 according to the first embodiment.

The aligned structure of cables 300 includes a combined cable 11 in which six cables 1 are covered with an insulative cover, a first cable core aligning insulator 2A, and a cable core fixing insulator 3. The first cable core aligning insulator 2A includes a lower first cable core aligning insulator 21 which aligns a part of the plurality of cable cores 5, and an upper first cable core aligning insulator 22 which is stacked on the lower first cable core aligning insulator 21 and aligns the remaining part of the plurality of cable cores 5. The first cable core aligning insulator 2A stacks and aligns a plurality of cable core exposed portions 5a vertically.

Cross sections of the cable cores 5 stacked and aligned in the two tiers by the first cable core aligning insulator 2A are exposed on a surface on the side of distal ends of the cable cores of the cable core fixing insulator 3. The cross sections are stacked and aligned in the two tiers.

A pitch $r_4$ is formed to be shorter than a pitch $r_1$. The pitch $r_4$ is a pitch of the exposed cross sections of the cable cores 5 of the cable core fixing insulator 3. The pitch $r_1$ is a pitch of the cables 1. In the aligned structure of cables 300 according to the third embodiment, it is preferable for the pitch $r_4$ to be substantially the same as a pitch $r_2$ and a pitch $r_3$. The pitch $r_2$ is a pitch of the cable cores 5 on the side of the cables 1 of the first cable core aligning insulator 2A. The pitch $r_3$ is a pitch of the cable cores 5 on the side of the cable core fixing insulator 3 of the first cable core aligning insulator 2A. That is, relationships among the pitches preferably satisfy $r_4=r_3=r_2<r_1$. In this case, it is necessary to narrow down a pitch of the cable cores 5 between end surfaces of the cables 1 and the first cable core aligning insulator 2A. However, each of grooves 6 of the first cable core aligning insulator 2A can be made parallel to each other. Alternatively, the pitch $r_4$ and the pitch $r_3$ are preferably formed the same, and the pitch $r_1$ and the pitch $r_2$ are preferably formed the same. That is, relationships among the pitches preferably satisfy $r_4=r_3<r_2=r_1$. In this case, the cable cores 5 can be made parallel to each other between the end surfaces of the cables 1 and the first cable core aligning insulator 2A. However, each of the grooves 6 of the first cable core aligning insulator 2A cannot be made parallel, since it is necessary to make the pitch on the side of the cable core fixing insulator 3 narrower than the pitch on the side of the cables 1. In each case, by at least making the pitch $r_4$ and the pitch $r_3$ the same, a pitch of the cable cores 5 in the cable core fixing insulator 3 becomes constant and it becomes easier to control the pitch $r_4$.

Next, a production method of the aligned structure of cables 300 according to the third embodiment will be described with reference to FIG. 10 and FIGS. 11A to 11G. FIG. 10 is a flowchart of production steps of the aligned structure of cables according to the third embodiment of the present invention. FIGS. 11A to 11G are schematic views for describing the production steps of the aligned structure of cables according to the third embodiment of the present invention.

Figure 11A:
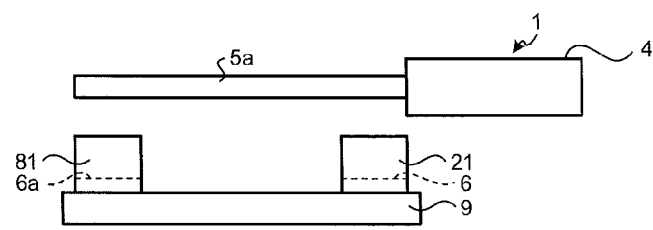
FIG. 11A is a schematic view for describing a production step of the aligned structure of cables according to the third embodiment of the present invention.
Figure 11B:
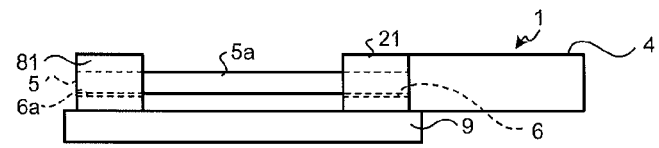
FIG. 11B is a schematic view for describing a production step of the aligned structure of cables according to the third embodiment of the present invention.

First, by stripping insulators 4 of the cables 1 over a prescribed length (step S21), the cable core exposed portions 5a are formed. As illustrated in FIGS. 11A and 11B, a part of the cable core exposed portions 5a, in this case three cable core exposed portions 5a, are fitted into grooves 6 of the lower first cable core aligning insulator 21 and grooves 6a of a lower second cable core aligning insulator 81, and the cables 1 are aligned (step S22).

Figure 11C:
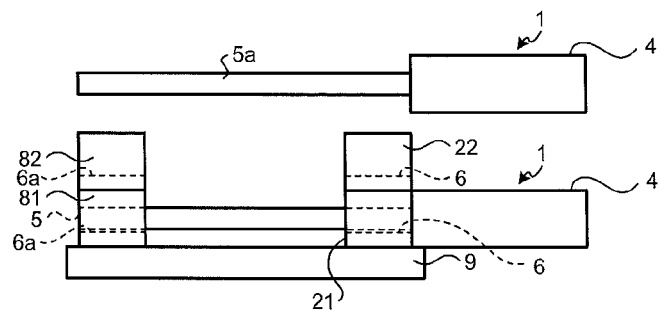
FIG. 11C is a schematic view for describing a production step of the aligned structure of cables according to the third embodiment of the present invention.
Figure 11D:
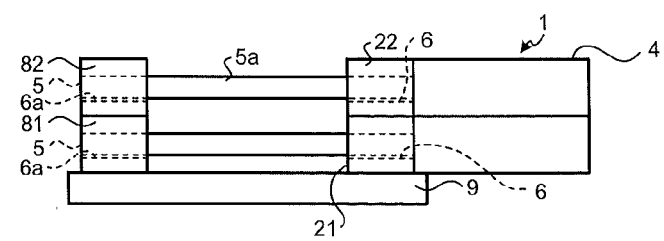
FIG. 11D is a schematic view for describing a production step of the aligned structure of cables according to the third embodiment of the present invention.

Next, as illustrated in FIG. 11C, the upper first cable core aligning insulator 22 and an upper second cable core aligning insulator 82 are stacked and arranged respectively on the lower first cable core aligning insulator 21 and the lower second cable core aligning insulator 81, and then, the remaining three cable core exposed portions 5a are fitted into grooves 6 of the upper first cable core aligning insulator 22 and grooves 6a of the upper second cable core aligning insulator 82, and the cables 1 are stacked and aligned in two tiers (step S23, see FIG. 11D).

Figure 11E:
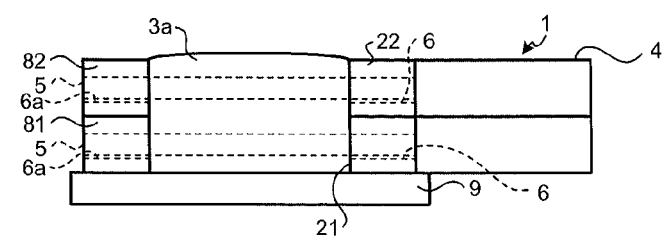
FIG. 11E is a schematic view for describing a production step of the aligned structure of cables according to the third embodiment of the present invention.
Figure 11F:
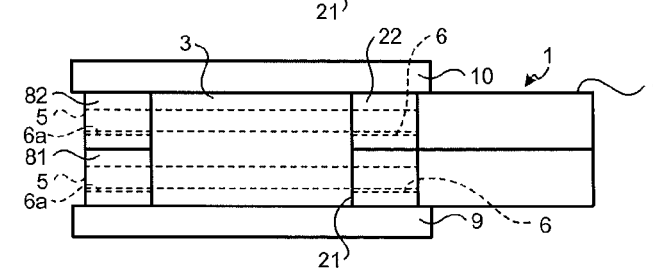
FIG. 11F is a schematic view for describing a production step of the aligned structure of cables according to the third embodiment of the present invention.

Then, on the periphery of the cable core exposed portions 5a stacked and aligned in the two tiers, a material 3a of the cable core fixing insulator 3 is applied (step S24, see FIG. 11E). While being fixed by an upper mold 10, the material is heated at an intended temperature and cured, whereby the cable core fixing insulator 3 is formed (step S25, see FIG. 11F).

Figure 11G:
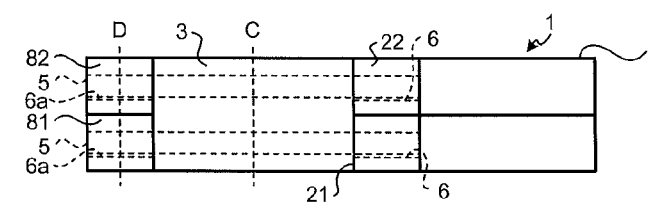
FIG. 11G is a schematic view for describing a production step of the aligned structure of cables according to the third embodiment of the present invention.

After the heating and curing, as illustrated in FIG. 11G, the upper mold 10 and a lower mold 9 are removed, and the cable core fixing insulator 3 is cut vertically at the position of the line C, whereby the aligned structure of cables 300, in which the cross sections of the cable cores 5 are exposed, is produced (step S26).

In the aligned structure of cables 300 according to the third embodiment, the pitch $r_4$ between the cable cores 5 can be made smaller than the pitch $r_1$ between the cables 1. Thus, the size of the aligned structure of cables 300 can be made further smaller. In addition, in the aligned structure of cables 300, the cable cores 5 of the cables 1 can be arranged sterically. Thus, it becomes possible to increase density and to save space further more.

In the third embodiment, the six cable cores 5 are stacked and aligned in the two tiers. However, there is no limit to the number of cable cores and the number of tiers. For example, the six cable cores may be stacked and aligned in three tiers, with two cable cores aligned in each tier.

Also, in the above, one aligned structure of cables 300 has been produced in one series of production steps. However, a plurality of aligned structures of cables 300 can be produced together. For example, a first cable core aligning insulator and a second cable core aligning insulator are formed to enable cable cores of a plurality of combined cables 11 to be aligned therein, and a cable core fixing insulator is formed to fix the cable cores 5 to align the plurality of combined cables 11 in a direction parallel to a longitudinal direction. Then, in a cutting step, after being cut in a direction vertical to a longitudinal direction of the cables 1 to expose the cross sections of the cable cores 5 on an end surface of the cable core fixing insulator, the cable core fixing insulator is cut in a direction parallel to the longitudinal direction of the cables 1, whereby the aligned structure of cables 300 including one combined cable 11 is produced.

Figure 12:
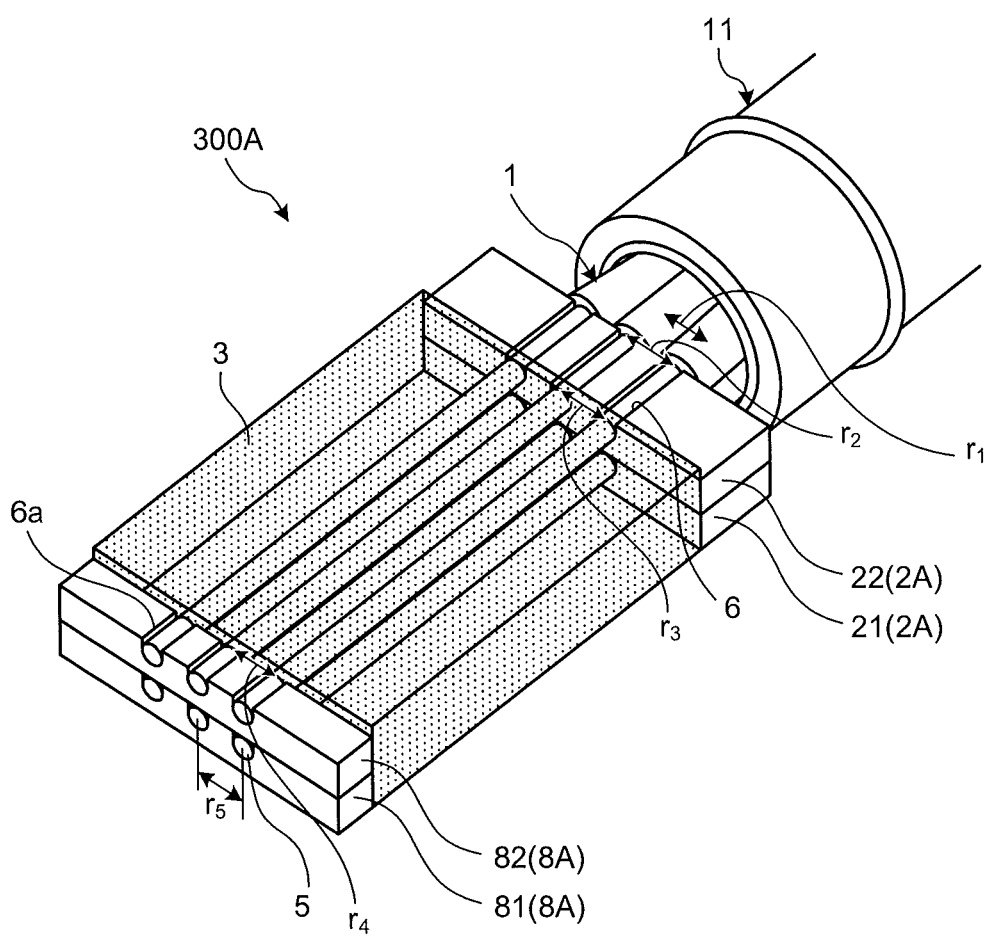
FIG. 12 is a perspective view illustrating an aligned structure of cables according to a modified example of the third embodiment of the present invention.

Furthermore, an aligned structure of cables may be produced by being cut in a direction vertical to a longitudinal direction of the cable cores 5, at the position of the line D of a second cable core aligning insulator 8A of FIG. 11G, to expose the cross sections of the cable cores 5. FIG. 12 is a perspective view illustrating an aligned structure of cables according to a modified example of the third embodiment of the present invention.

An aligned structure of cables 300A according to the modified example includes a second cable core aligning insulator 8A arranged on the side of distal ends of the cable cores 5 of the cable core fixing insulator 3. The second cable core aligning insulator 8A includes a lower second cable core aligning insulator 81 which aligns a part of the plurality of cable cores 5, and an upper second cable core aligning insulator 82 which is stacked on the lower second cable core aligning insulator 81 and aligns the remaining part of the plurality of cable cores 5. The second cable core aligning insulator 8A stacks and aligns a plurality of cable core exposed portions 5a vertically.

In the aligned structure of cables 300A according to the modified example, the pitch $r_5$ between the cable cores 5 can be made smaller than the pitch $r_1$ between the cables 1. Thus, the size of the aligned structure of cables 300A can be made further smaller. In addition, since the second cable core aligning insulator 8A, in which the pitch of the cross sections of the cable cores 5 has been set in advance, is used, positional accuracy of the cross sections of the cable cores 5 can be improved. Moreover, in the aligned structure of cables 300A, the cable cores 5 of the cables 1 can be arranged sterically. Thus, it becomes possible to increase density and to save space further more.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An aligned structure of cables, comprising:
   a plurality of cables, each of the plurality of cables including:
      a first portion having a conductive cable core and an insulator covering an outer periphery of the cable core; and
      a second portion distal to the first portion in which the insulator covering is removed to form a cable core exposed portion to expose the cable core;
   a cable core aligning insulator having a distal side and a proximal side, the cable core aligning insulator including a plurality of grooves extending from the proximal side of the cable core aligning insulator to the distal side of the cable core aligning insulator, the second portion of each of the plurality of cables are fitted into a respective one of the plurality of grooves to align each of the second portions; and a cable core fixing insulator having a distal side and a proximal side, the cable core fixing insulator fixes the second portions aligned by the first cable core aligning insulator, wherein cross sections of the cable cores are exposed on a surface on the distal side of the cable core fixing insulator, and a pitch of the cross sections at the distal side of the cable core fixing insulator is shorter than a pitch of the plurality of cables proximal to the proximal side of the first cable core aligning insulator.

2. An aligned structure of cables, comprising:

a plurality of cables, each of the plurality of cables including:
 a first portion having a conductive cable core and an insulator covering an outer periphery of the cable core; and
 a second portion distal to the first portion in which the insulator covering is removed to expose the cable core;

a first cable core aligning insulator having a distal side and a proximal side, the first cable core aligning insulator including a plurality of first grooves extending from the proximal side of the first cable core aligning insulator to the distal side of the first cable core aligning insulator, the second portion of each of the plurality of cables are fitted into a respective one of the plurality of first grooves to align each of the second portions;

a cable core fixing insulator having a distal side and a proximal side, the cable core fixing insulator fixes the second portions aligned by the first cable core aligning insulator, and a second cable core aligning insulator having a distal side and a proximal side, the second cable core aligning insulator being arranged on the distal side of the cable core fixing insulator, the second cable core aligning insulator includes a plurality of second grooves extending from the proximal side of the second cable core aligning insulator to the distal side of the second cable core aligning insulator, the second portion of each of the plurality of cables are fitted into a respective one of the plurality of second grooves to align each of the second portions, wherein a pitch of the second portions at the distal side of the cable core fixing insulator is shorter than a pitch of the plurality of cables proximal to the proximal side of the first cable core aligning insulator; and cross sections of the cable cores are exposed on a surface on the distal side of the second cable core aligning insulator, and a pitch of the cross sections is substantially the same as the pitch of the second portions at the distal side of the cable core fixing insulator.

3. The aligned structure of cables according to claim 2, wherein beveled portions are formed on both ends in an alignment direction on the distal side, on which the cross sections of the cable cores are exposed, of the second cable core aligning insulator.

4. The aligned structure of cables according to claim 1, wherein the cable core aligning insulator includes a lower cable core aligning insulator which aligns a part of the cable cores and an upper cable core aligning insulator which is stacked on the lower cable core aligning insulator and aligns a remaining part of the cable cores, and the cable core aligning insulator stacks and aligns the second portions vertically.

5. The aligned structure of cables according to claim 2, wherein the first and second cable core aligning insulators include a lower cable core aligning insulator which aligns a part of the cable cores and an upper cable core aligning insulator which is stacked on the lower cable core aligning insulator and aligns a remaining part of the cable cores, and the second cable core aligning first and second cable core aligning insulators include stack and align the second portions vertically.

6. The aligned structure of cables according to claim 1, wherein beveled portions are formed on both ends in an alignment direction on the distal side, on which the cross sections of the cable cores are exposed, of the cable core fixing insulator.

* * * * *